United States Patent
Gotkis et al.

(10) Patent No.: US 7,084,621 B2
(45) Date of Patent: Aug. 1, 2006

(54) ENHANCEMENT OF EDDY CURRENT BASED MEASUREMENT CAPABILITIES

(75) Inventors: Yehiel Gotkis, Fremont, CA (US); Rodney Kistler, Los Gatos, CA (US); Aleksander Owczarz, San Jose, CA (US); David Hemker, San Jose, CA (US); Nicolas J. Bright, San Jose, CA (US)

(73) Assignee: Lam Research Corporation, Fremont, CA (US)

( * ) Notice: Subject to any disclaimer, the term of this patent is extended or adjusted under 35 U.S.C. 154(b) by 333 days.

(21) Appl. No.: 10/256,055

(22) Filed: Sep. 25, 2002

(65) Prior Publication Data

US 2004/0058545 A1    Mar. 25, 2004

(51) Int. Cl.
*G01B 7/06* (2006.01)
(52) U.S. Cl. ........................... 324/229; 324/231
(58) Field of Classification Search ........ 324/219–223, 324/228–232, 237–243
See application file for complete search history.

(56) References Cited

U.S. PATENT DOCUMENTS

| | | | |
|---|---|---|---|
| 3,815,016 A | 6/1974 | Nix et al. | 324/34 |
| 4,556,845 A | 12/1985 | Strope et al. | |
| 4,706,020 A * | 11/1987 | Viertl et al. | 324/238 |
| 5,473,247 A | 12/1995 | You et al. | 324/227 |
| 5,485,082 A | 1/1996 | Wisspeintner et al. | 324/202 |
| 5,537,038 A * | 7/1996 | Ando | 324/253 |
| 5,559,428 A | 9/1996 | Li et al. | |
| 5,660,672 A | 8/1997 | Li et al. | 156/345 |
| 5,731,697 A | 3/1998 | Li et al. | |
| 5,889,401 A | 3/1999 | Jourdain et al. | |
| 5,926,020 A | 7/1999 | Samson | 324/238 |
| 6,072,313 A | 6/2000 | Li et al. | |
| 6,265,870 B1 | 7/2001 | Weischedel | 324/240 |
| 6,291,992 B1 | 9/2001 | Van Andel et al. | 324/240 |
| 6,563,308 B1 | 5/2003 | Nagano et al. | 324/230 |

FOREIGN PATENT DOCUMENTS

| | | | | |
|---|---|---|---|---|
| DE | GB 1 452 417 | 10/1976 | | 7/10 |
| EP | 0 370 691 | 5/1990 | | 27/90 |
| EP | 0 459 441 | 5/1991 | | 27/90 |

* cited by examiner

*Primary Examiner*—Bot LeDynh
(74) *Attorney, Agent, or Firm*—Martine Penilia & Gencarella, LLP

(57) ABSTRACT

A method and an apparatus for enhancement of the for measuring resistance-based features of a substrate is provided. The apparatus includes a sensor configured to detect a signal produced by a eddy current generated electromagnetic field. The magnetic field enhancing source is positioned to the alternative side of the object under measurement relative to the sensor to enable the sensitivity enhancing action. The sensitivity enhancing source increases the intensity of the eddy current generated in the object under measurement, and as a result the sensitivity of the sensor. A system enabled to determine a thickness of a layer and a method for determining a resistance-based feature characteristic are also provided.

27 Claims, 9 Drawing Sheets

ENHANCEMENT OF EDDY CURRENT BASED MEASUREMENT CAPABILITIES

CROSS REFERENCE TO RELATED APPLICATION

This application is related to U.S. patent application Ser. No. 10/186,472, entitled "INTEGRATION OF EDDY CURRENT SENSOR BASED METROLOGY WITH SEMICONDUCTOR FABRICATION TOOLS" and U.S. patent application Ser. No. 10/186,932 entitled "METHOD AND APPARATUS OF ARRAYED SENSORS FOR MIETROLOGICAL CONTROL" both applications filed on Jun. 28, 2002. The disclosure of these related applications are incorporated herein by reference.

BACKGROUND OF THE INVENTION

The invention relates generally to integrated circuit fabrication and more specifically to metrology for process control during semiconductor wafer manufacturing.

During semiconductor fabrication there are many opportunities for measuring features of substrates undergoing processing operations. Many of the features can be determined by capturing a signal indicating the feature. For example, various end point determination methods are available that employ laser interferometry, optical emission, etc. However, as the features continue to decrease in size, especially the thickness of films employed in the manufacture of semiconductors, the signals that are indicative of the feature become undetectable in certain situations. For example, eddy current sensors are used for displacement, proximity and film thickness measurements. The sensors rely on the induction of current in a sample by the fluctuating electromagnetic field of a test coil proximate to the object being measured. Fluctuating electromagnetic fields are created as a result of passing an alternating current through the coil. The fluctuating electromagnetic fields induce eddy currents which perturb the applied field and change the coils inductance.

FIG. 1 is a simplified schematic diagram of the principle upon which an eddy current sensor operates. An alternating current flows through coil 100 in close proximity to conducting object 102. The electromagnetic field of the coil induces eddy currents 104 in conducting object 102. The magnitude and the phase of the eddy currents in turn effect the loading on the coil. Thus, the impedance of the coil is impacted by the eddy currents. This impact is measured to sense the proximity of conducting object 102 as well as a thickness of the object. Distance 106 impacts the effect of eddy currents 104 on coil 100, therefore, if object 1002 moves, the signal from the sensor monitoring the impact of eddy currents on coil 100 will also change.

Attempts to use eddy current sensors to measure thickness of a thin film, especially a copper thin film, have been unsuccessful. The eddy current sensors have been found to be blind to films having a thickness less than about 2500 Angstroms (Å). Accordingly, as feature sizes continue to decrease, eddy current sensors must be able to be adapted to sense thin films less than about 2500 Å. In addition, thickness measurement sensors currently available are generally designed to measure the thickness of a particular layer of a layer stack. That is, the sensors are specifically designed to measure thickness solely and do not have the flexibility to perform other measurements besides thickness measurements. More particularly, the thickness measurement sensors do not have the capability of selectively enhancing a thickness measurement for a particular layer of a stack of layers disposed over a substrate.

In view of the foregoing, there is a need to enhance the sensitivity of eddy current sensors to allow for the measurement of thin films. Additionally, there is a need to provide a sensor capable of selectively targeting a film of a layer stack.

SUMMARY OF THE INVENTION

Broadly speaking, the present invention fills these needs by increasing the sensitivity of a sensor, such as an eddy current sensor, by enhancing a magnetic field that impacts the magnitude of a signal being measured, such as an eddy current. It should be appreciated that the present invention can be implemented in numerous ways, including as an apparatus, a system, a device, or a method. Several inventive embodiments of the present invention are described below.

In accordance with one embodiment, a method for determining a resistance-based property is provided. The method initiates with providing a sensor configured to detect signal intensity variations correlated to a magnetic field. Then, a conductive object is introduced into a detection space of the sensor. Next, a primary magnetic field generated by the sensor is enhanced through a magnetic field enhancing source to increase the sensitivity and the signal to noise ratio of the sensor.

In accordance with another embodiment of the present invention, an apparatus for measuring resistance-based properties of a conductive object is provided. The apparatus includes a sensor configured to detect a signal produced by a magnetic field. A magnetic field enhancing source is included. The magnetic field enhancing source is positioned relative to the sensor to enable a conductive object to be placed in a detection space between the sensor and the magnetic field enhancing source. The magnetic field enhancing source increases a sensitivity of the sensor.

In yet another embodiment, a system enabled to determine a thickness of a layer of an object through a signal generated by a magnetic field is provided. The system includes an eddy current sensor. A magnetic field enhancing source positioned to define a detection space between the eddy current sensor and the magnetic field enhancing source is included. The magnetic field enhancing source is positioned so as to intersect an axis of the eddy current sensor. A base configured to support an object such that the object is positioned within the detection space between the eddy current sensor and the magnetic field enhancing source. A controller in communication with the eddy current sensor is provided. The controller is configured to output a thickness of a layer of the object from a signal detected by the eddy current sensor, wherein the sensitivity of the eddy current sensor is increased by the magnetic field enhancing source.

In accordance with still yet another embodiment of the present invention, a system enabled to determine a thickness of a layer of a substrate is provided. The system includes a substrate support configured to support a bottom surface of a substrate. The substrate support includes a magnetic field enhancing source. An eddy current sensor positioned above the substrate support is included. A controller in communication with the eddy current sensor is provided. The controller is configured to output a thickness of a layer of the substrate from a signal detected by the eddy current sensor, wherein the sensitivity of the eddy current sensor to the signal is increased by the magnetic field enhancing source.

It is to be understood that the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate exemplary embodiments of the invention and together with the description serve to explain the principles of the invention.

DETAILED DESCRIPTION OF THE PREFERRED EMBODIMENTS

Figure 1:
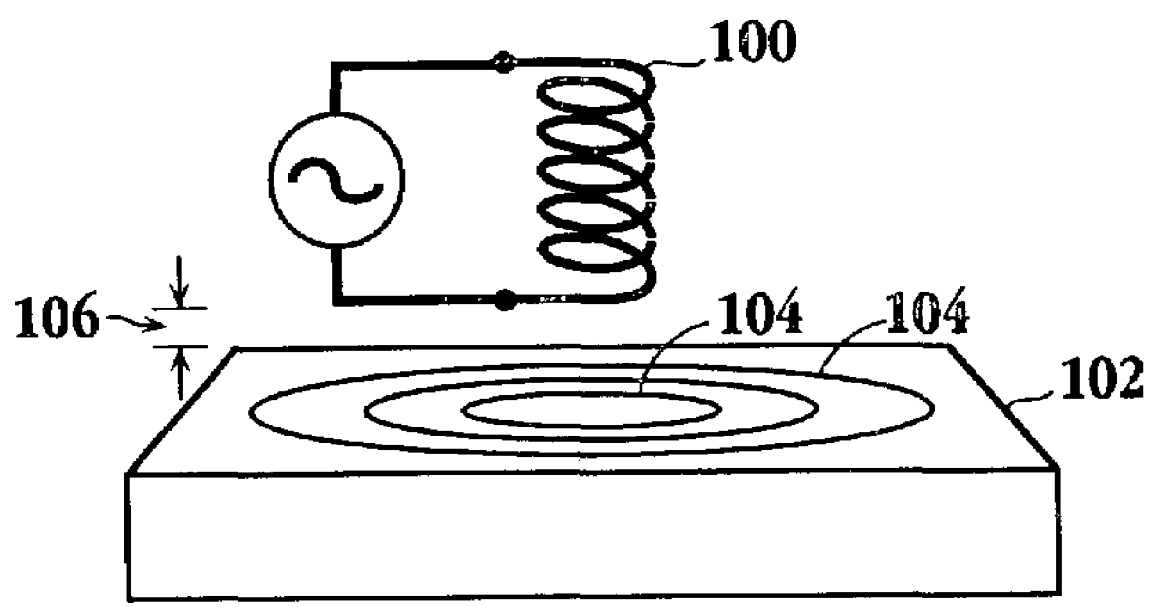
FIG. 1 is a simplified schematic diagram of the principle upon which an eddy current sensor operates.

Several exemplary embodiments of the invention will now be described in detail with reference to the accompanying drawings. FIG. 1 is discussed above in the "Background of the Invention" section. It should be appreciated that the term "about" as used herein refers to a range of +/−10%.

The embodiments described herein allow for the enhancement of a resistance-based signal, such as an eddy current, by externally enhancing the magnetic field within the tested object, which in turn increases the eddy current. The increased eddy current then enhances the sensor's sensitivity. The coherent amplification of the magnetic field enhances the signal being detected so that a sensor is capable of detecting the signal to provide the necessary information to determine a resistance-based property, i.e., feature characteristic, of an object. Some exemplary resistance-based properties include thickness of a layer, thickness of a semiconductor substrate, dopant concentration of the substrate, film stack composition, thin conductive film integrity, surface roughness of a conductive layer, distribution of impurities in a conductive layer and grain size distribution within a conductive layer, etc.

In one embodiment, the sensor is an eddy current sensor and the resistance-based feature characteristic being monitored is the thickness of a film. The increased sensitivity of the eddy current sensors allows for the measurement of thin films that the sensor was previously not capable of "seeing." In one embodiment, the thin film thickness is less than about 2500 angstroms (Å). In another embodiment, the magnetic field is enhanced by a magnetic field enhancing source, such as ferromagnetic material, paramagnetic material or even an additional eddy current sensor. Thus, a substrate placed between the eddy current sensor and the magnetic field enhancing source will generate an eddy current that is detectable by the eddy current sensor through the enhancement of the magnetic field generating the eddy current sensor. The detected eddy current is indicative of the thickness of a thin film of the substrate or some other resistance-based feature characteristic. It should be appreciated that the terms substrate and wafer are interchangeable as used herein.

Figure 2:
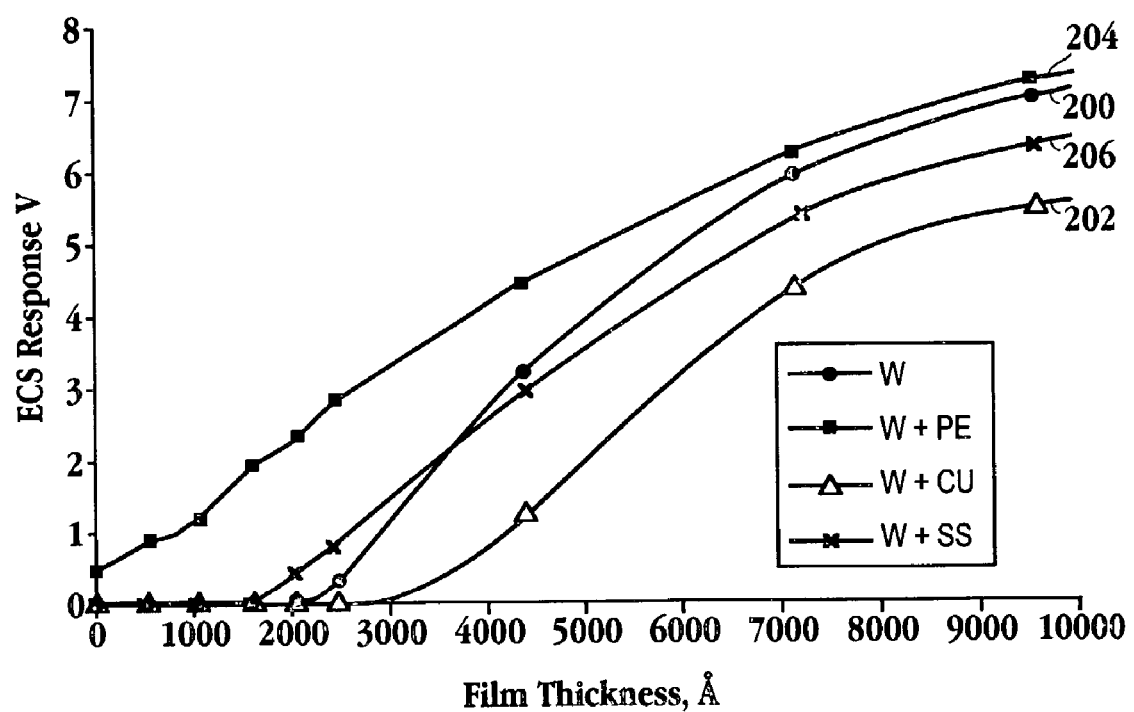
FIG. 2 is a graph illustrating the eddy current sensor response to various configurations in accordance with one embodiment of the invention.

FIG. 2 is a graph illustrating the eddy current sensor response to various configurations in accordance with one embodiment of the invention. Line 200 represents the eddy current sensor response with just a wafer alone without a magnetic field enhancing source. As can be seen, the eddy current sensor is blind to thickness below 2500 Angstroms. In other words, with this particular sensitivity the eddy current sensor is incapable of detecting films less than 2500 Angstroms. Line 202 represents the eddy current sensor response when a copper slug is placed on the alternative side of the wafer, i.e., directed at the opposite side of the wafer as compared to the eddy current sensor. It should be appreciated that copper is a diamagnetic material. Accordingly, when a diamagnetic material is placed behind the measured film, it produces a secondary magnetic field, which suppresses the sensor's primary field. Diamagnetic materials have no permanent magnetic dipole moments, but have dipoles induced by an applied magnetic field. In turn, the eddy current sensor signal is decreased. Thus, the eddy current sensor becomes less sensitive when a diamagnetic material is placed on the alternative side of the wafer from the sensor. Line 204 represents the eddy current sensor response when a ferromagnetic material is placed on the alternative side of the wafer. The presence of the ferromagnetic material enhances the eddy current sensor signal making it possible for the eddy current sensor to see and to measure film thickness for very thin films significantly below 2500 Angstroms.

One skilled in the art will appreciate that ferromagnetism is a property of a material that enables the material to become a permanent magnet, i.e., ferromagnetic materials when placed in a magnetic field develop a very strong internal field and retains some of it when the external field is removed. As is generally known, ferromagnetism is caused by the unbalanced spin of atomic electrons which creates a magnetic dipole moment having the effect of a tiny magnet. The most common ferromagnetic substances are iron, cobalt, nickel and alloys of each of these metals, such as permalloy. A paramagnetic material will also impart the same effect as the ferromagnetic material. As is generally known, paramagnetic materials exhibit moderate attraction into a magnetic field, caused by the presence of unpaired electrons. Paramagnetism is very common in the gas phase and in solutions of many transition metal compounds, where the unpaired electrons arise because several orbitals lie at the same energy level. Paramagnetic materials include oxygen and ions of various metals such as magnesium, gadolinium, aluminum, etc.

Returning to FIG. 2, line 206 represents the eddy current sensor response when a stainless steel slug is placed on the alternative side of the wafer. As illustrated, the stainless steel has a slight enhancing effect allowing layers as thin as 1500 angstroms to be seen by the sensor. As stainless steel is made up of a number of elements, which may be present in varying amounts, the composition of the stainless steel will have an impact on the enhancement of the eddy current signal since different compositions have different magnetic properties. As will be explained further below, the stainless steel backing of a chemical mechanical planarization polishing pad may be a magnetic field enhancing source. It should be appreciated that a magnetic field enhancing source may also be referred to as an eddy current enhancing source, since the eddy currents are enhanced through the enhancement of the magnetic field generating the eddy currents in one embodiment of the invention. In this embodiment, the eddy current sensor is embedded in the wafer carrier of a chemical mechanical planarization system as described with reference to FIG. 7.

Figure 3:
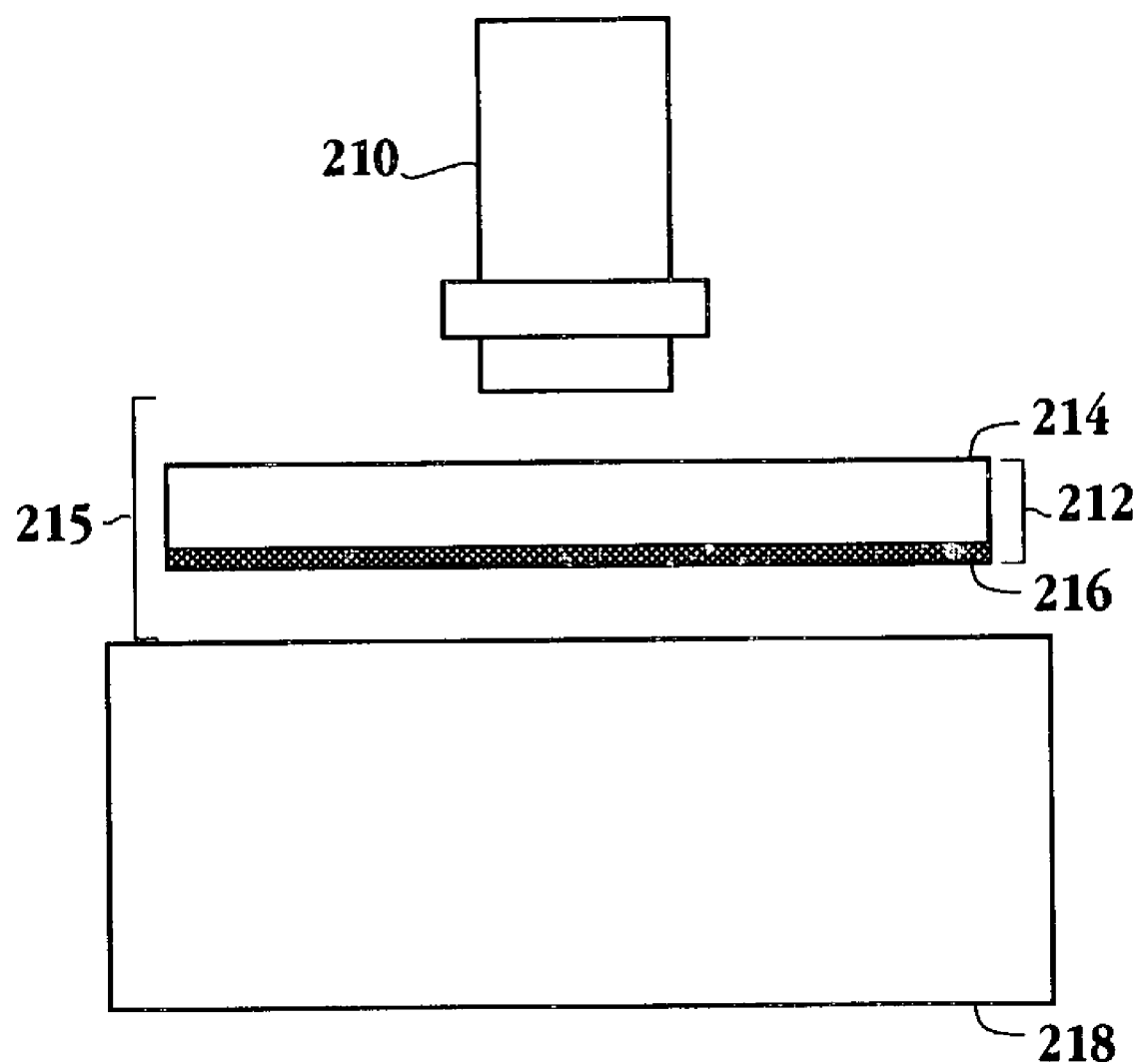
FIG. 3 is a simplified schematic diagram of a substrate placed in between an eddy current sensor and a magnetic field enhancing source in accordance with one embodiment of the invention.

FIG. 3 is a simplified schematic diagram of a substrate placed in between an eddy current sensor and a magnetic field enhancing source in accordance with one embodiment of the invention. Substrate 212, consisting of doped silicon portion 214 and thin film 216, is positioned in detection space 215. It should be appreciated that detection space 215 can also be referred to as a detection region. Detection space 215 is defined between eddy current sensor 210 and a top surface of magnetic field enhancing source 218. Magnetic field enhancing source may be a paramagnetic material or a ferromagnetic material. As paramagnetic and ferromagnetic materials are magnetized in the direction of the primary field, the eddy currents generated in substrate 212 are enhanced through the enhancement of the magnetic field generating the eddy current. Thus, the sensor sensitivity, especially in the thin film range, is enhanced drastically, i.e., by orders of magnitude. In addition, the signal to noise ratio of the sensor is also enhanced. In one embodiment, thin film 216 has a thickness of less than 2500 angstroms.

The configuration of FIG. 3 shows eddy current sensor 210 positioned closest to main substrate 214 while magnetic field enhancing source 218 is positioned closest to thin film 216. That is, eddy current sensor 210 and magnetic enhancing source 218 are positioned on alternative sides of substrate 212. Where the substrate includes multiple layers, i.e., more than one layer, magnetic field enhancing source 218 enhances the signal indicating the thickness of the layer closest to the magnetic field enhancing source. In reference to FIG. 3, magnetic field enhancing source 218 enhances the signal for determining the thickness of thin film 216 when thin film 216 is the film closest to the magnetic field enhancing source. Thus, through the use of magnetic field-enhancing source 218, the selective enhancement of a layer or film of substrate 212 is achievable. Consequently, magnetic field enhancing source 218 act as a magnetic projector which utilizes the magnetic field that passes through thin film 216 to irradiate the thin film by reflecting the magnetic field back toward the sensor and favorably orienting the magnetic field. The favorable orientation of the magnetic field allows for the enhancement of the strength of the eddy current, as well as the signal to noise ratio, so that sensor 210 can detect the signal. It should be appreciated that the favorable orientation of the magnetic field is accomplished through a ferromagnetic or paramagnetic material used as magnetic field enhancing source 218 in one embodiment.

Figure 4:
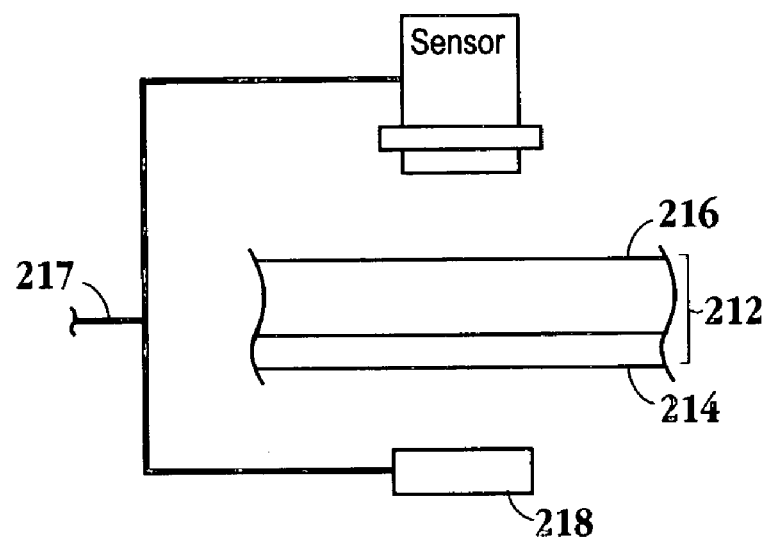
FIG. 4 is a simplified schematic diagram of an alternative embodiment to FIG. 3 where a sensor and a magnetic field enhancing source are coupled together.

FIG. 4 is a simplified schematic diagram of an alternative embodiment to FIG. 3 where a sensor and a magnetic field enhancing source are coupled together. Here, sensor 210 is closest to thin film 216 while magnetic field enhancing source 218 is closest to main substrate 214. In this embodiment, the orientation of substrate 212 has been reversed. It should be appreciated that sensor 210 and magnetic field enhancing source 218 can be rigidly connected so that the sensor in the magnetic field enhancing source may be moved in unison by arm 217. For example, sensor 210 and magnetic field enhancing source 218 may be used with some front end semiconductor fabrication tools, such as mappers, aligners, etc., as explained with reference to FIG. 8. Here, the mapper or the aligner rotate substrate 212 while arm 217 is enabled to move sensor 210 in magnetic field enhancing source 218 in a radial direction. Thus, the entire surface of substrate 212 can be mapped in this configuration. As the orientation of substrate 212 has been reversed, magnetic field enhancing source 218 is closest to main substrate 214, therefore, the magnetic field that passes through main substrate 214 is used to irradiate the main substrate by reflecting the magnetic field back toward the sensor and favorably orienting the magnetic field. Where main substrate 214 is a doped silicon substrate, the configuration of FIG. 4 may be used to monitor a resistance-based property. For example, a dopant concentration of the silicon substrate is capable of being measured. One skilled in the art will appreciate that this configuration may be employed after a doping operation to verify if the correct dopant concentration was achieved. In another embodiment, the configuration of FIG. 4 is used for endpoint determination of the doping operation. It should be appreciated that any of the resistance-based properties, also referred to as resistance-based feature characteristics, mentioned above, may be quantified. Furthermore, while semiconductor substrates are referred to herein, the invention may be extended to any conductive object being evaluated through a signal correlated to a magnetic field.

Figure 5:
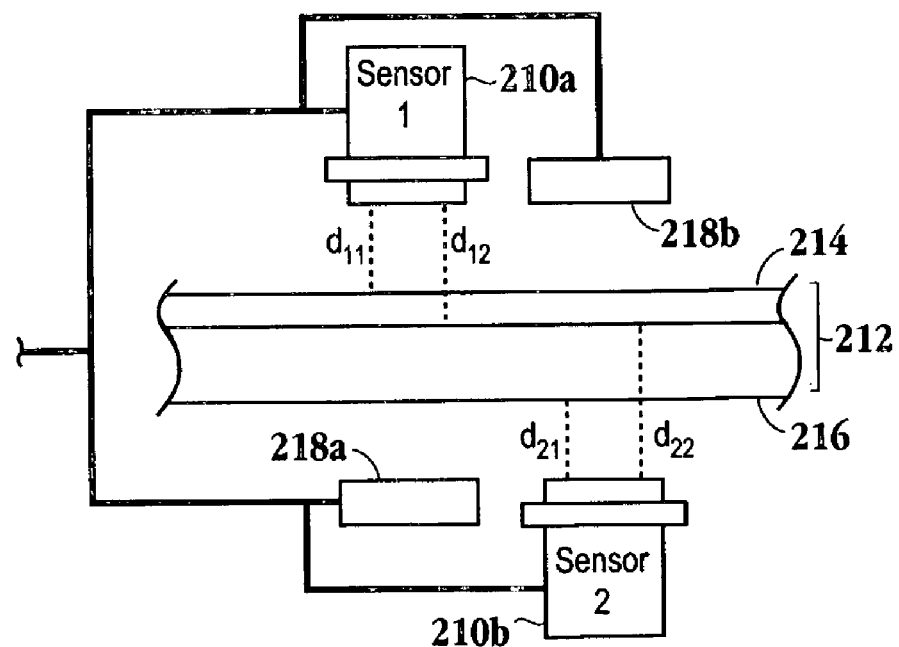
FIG. 5 is a simplified schematic where multiple sensors enable scanning of the top and bottom surfaces of a substrate in accordance with one embodiment of the invention.

FIG. 5 is a simplified schematic where multiple sensors enable scanning of the top and bottom surfaces of a substrate in accordance with one embodiment of the invention. Here, sensor 1 210a is positioned closest to main substrate 214, while sensor 2 210b is positioned on an alternate side of substrate 212. Accordingly, magnetic field enhancing sources 218a and 218b are located on opposite sides of substrate 212. It will be apparent to one skilled in the art that in this embodiment, there is no need to flip, i.e., reverse the orientation of, substrate 212 in order to measure from both sides of the substrate. Here again, this configuration can be used on semiconductor manufacturing process tools such as mappers, aligners, etc. The data gathered from the mapper or the aligner can be stored and later considered to set a recipe for a downstream process such as etching deposition or chemical mechanical planarization. Alternatively, the configuration of FIG. 5 is used as an endpoint determination for a semiconductor fabrication process. In one embodiment, the sensor configuration of FIG. 3, 4, or 5 is placed in a substrate path of a semiconductor fabrication tool and records the appropriate measurements while the substrate is being moved from one station to another station of the semiconductor fabrication process tool.

Figure 6:
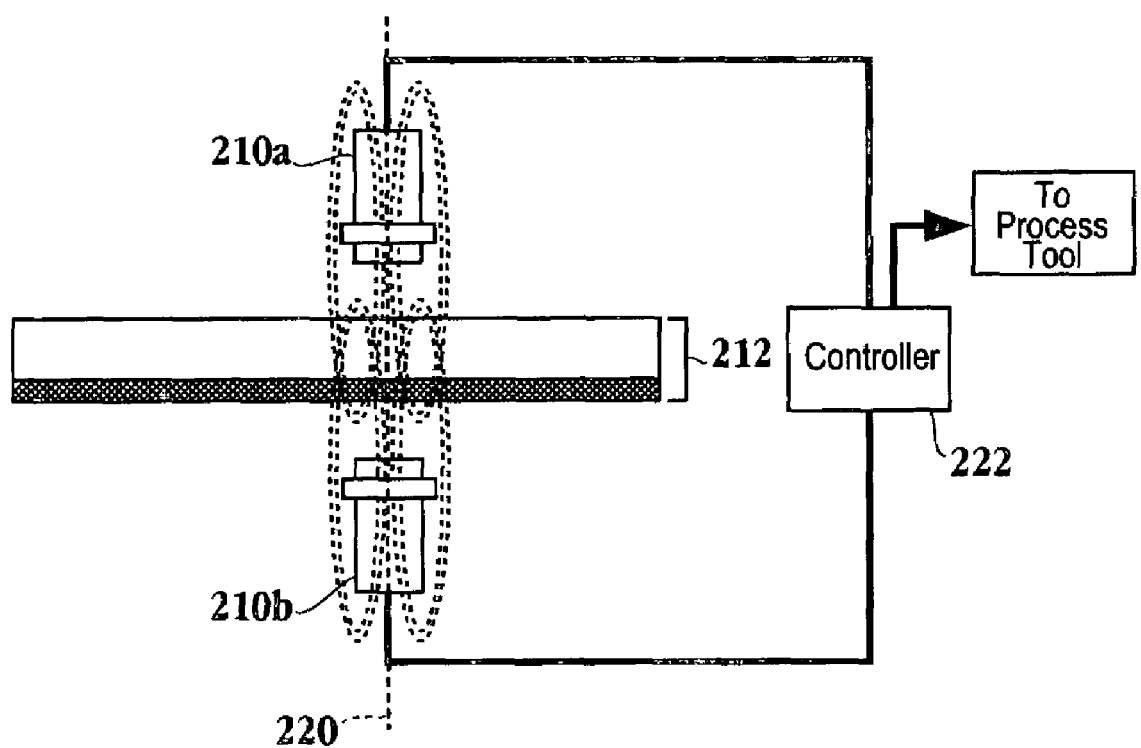
FIG. 6 is a simplified schematic diagram where eddy current sensors placed on opposite sides of a substrate are used to enhance a signal detected by one of the eddy current sensors in accordance with one embodiment of the invention.

FIG. 6 is a simplified schematic diagram where eddy current sensors placed on opposite sides of a substrate are used to enhance a signal detected by one of the eddy current sensors in accordance with one embodiment of the invention. Here, substrate 212 is within the detection region defined between upper eddy current sensor 210a and lower eddy current sensor 210b. Eddy current sensor 210a is substantially aligned with eddy current sensor 210b. That is, eddy current sensor 210a and eddy current sensor 210b share a common axis 220 in one embodiment of the invention. The signal data gathered by eddy current sensors 210a and 210b is communicated to controller 222. Controller 222 is configured to quantify the data from the signals so that the appropriate resistivity based feature characteristic can be determined and output to a process tool, if necessary. Alternatively, the data is electronically stored on storage media associated with controller 222.

Figure 7:
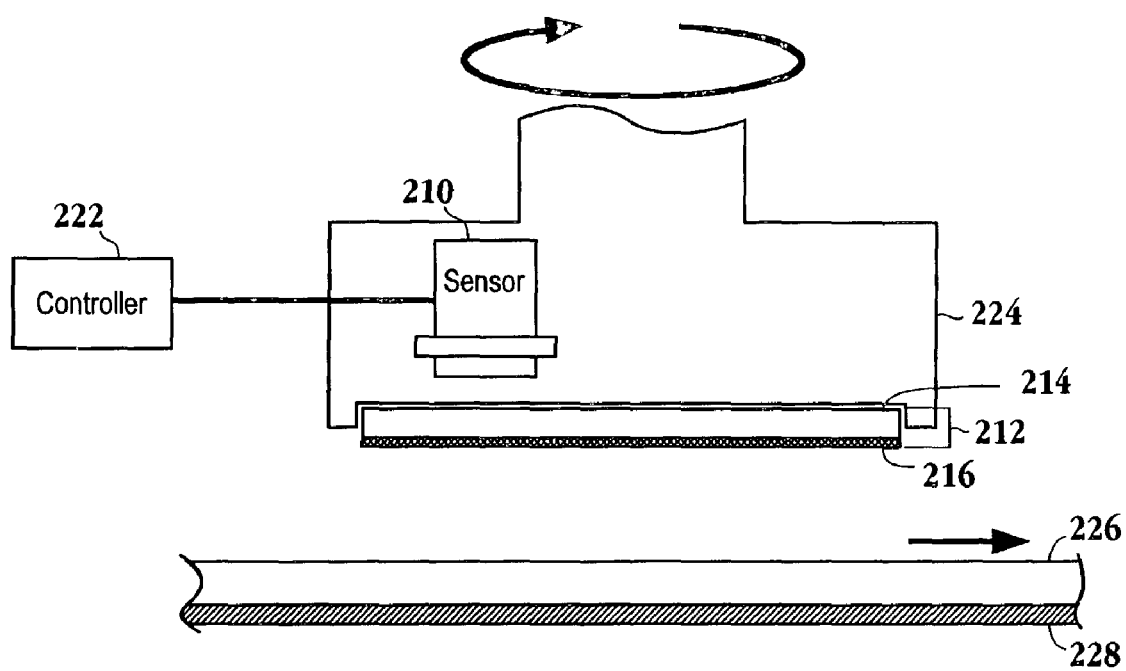
FIG. 7 is a simplified schematic diagram of a chemical mechanical planarization (CMP) system configured to enhance the sensitivity of a sensor in accordance with one embodiment of the invention.

FIG. 7 is a simplified schematic diagram of a chemical mechanical planarization (CMP) system configured to enhance the sensitivity of a sensor in accordance with one embodiment of the invention. Sensor 210 is embedded in substrate carrier 224. Substrate carrier 224 is configured to support substrate 212 having a main substrate portion 214 and a thin film 216. Sensor 210 is in communication with controller 222. In one embodiment sensor 210 is an eddy current sensor. Of course, controller 222 can be a general purpose computer having a memory containing a recipe for the chemical mechanical planarization operation. During the CMP operation, substrate carrier 224 brings substrate 212 into contact with the top surface of planarization pad 226. Planarization pad 226 is supported by stainless steel backing 228. Here, stainless steel backing 228 can act as a magnetic field enhancing source as described above. Of course, stainless steel backing 228 could include or be replaced by another metal having ferromagnetic or paramagnetic properties to further enhance the sensitivity sensor 210. Consequently, the sensitivity and the signal to noise ratio of sensor 210 will be increased to enable the sensor to detect thin films, i.e., having a thickness less than 2500 angstroms. It will be apparent to one skilled in the art that the hysteresis effect is avoided where stainless steel is replaced with a ferromagnetic material or paramagnetic material suitable for the CMP operation. It should be appreciated that while the CMP system of FIG. 7 is illustrated as a linear belt system, the embodiments described herein can also be applied to a rotary table top CMP system.

Figure 8:
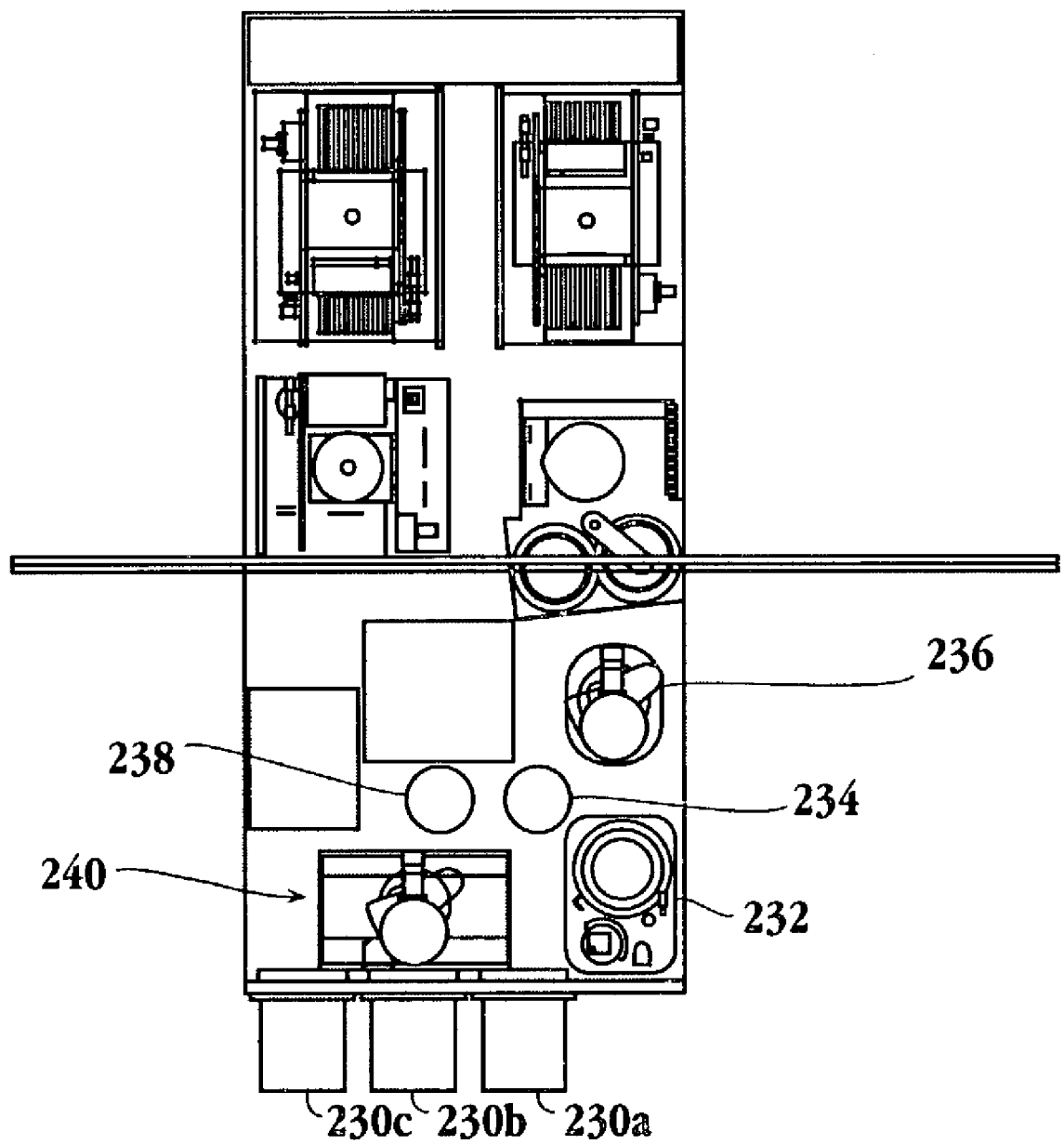
FIG. 8 is a high level schematic of a semiconductor processing tool, such as a CMP system, in accordance with one embodiment of the invention.

FIG. 8 is a high level schematic of a semiconductor processing tool, such as a CMP system, in accordance with one embodiment of the invention. As will be described below, the sensor and magnetic field enhancing device as described with reference to FIGS. 3–6, are incorporated into the front end of the CMP processing system to provide a thickness profile of the wafers as they are delivered to the processing module or received from the processing module. Load port modules 230a, 230b, and 230c contain wafers to be processed and/or wafers that have been processed. Robot 240 is configured to access load port modules 230a–c to transport the wafers to another station, such as dry buffer 238 or aligner 234. Robot 236 transports the wafer to and from the CMP processing module. Region 232 represents a spin, rinse and dry (SRD) module. It should be appreciated that a suitable sensor, such as the eddy current sensors discussed with reference to FIGS. 4-7, can be integrated within the front end system of FIG. 8 in one embodiment. For example, the sensor or even an array of sensors can be integrated with aligner 234. Accordingly, as aligner 234 rotates the wafer, the thickness profile is detected by the sensor or sensors. For example the embodiments described with reference to FIGS. 4–6 are configured to move radially over the spinning substrate to provide a map of the entire surface of the substrate. Thus, no additional space is required, i.e., the footprint of the system is not affected, and the pathway of the wafer is not altered to obtain the information. While the sensor configuration is discussed with respect to a CMP tool, it should be appreciated that the sensor configuration can be incorporated with any tools dealing with thin metal films and using wafer aligners or mappers. Furthermore, a single sensor can be incorporated into the embodiments described herein, or alternatively, an array of sensors can be incorporated to cover a larger area for a more complete thickness profile of a wafer.

Figure 9:
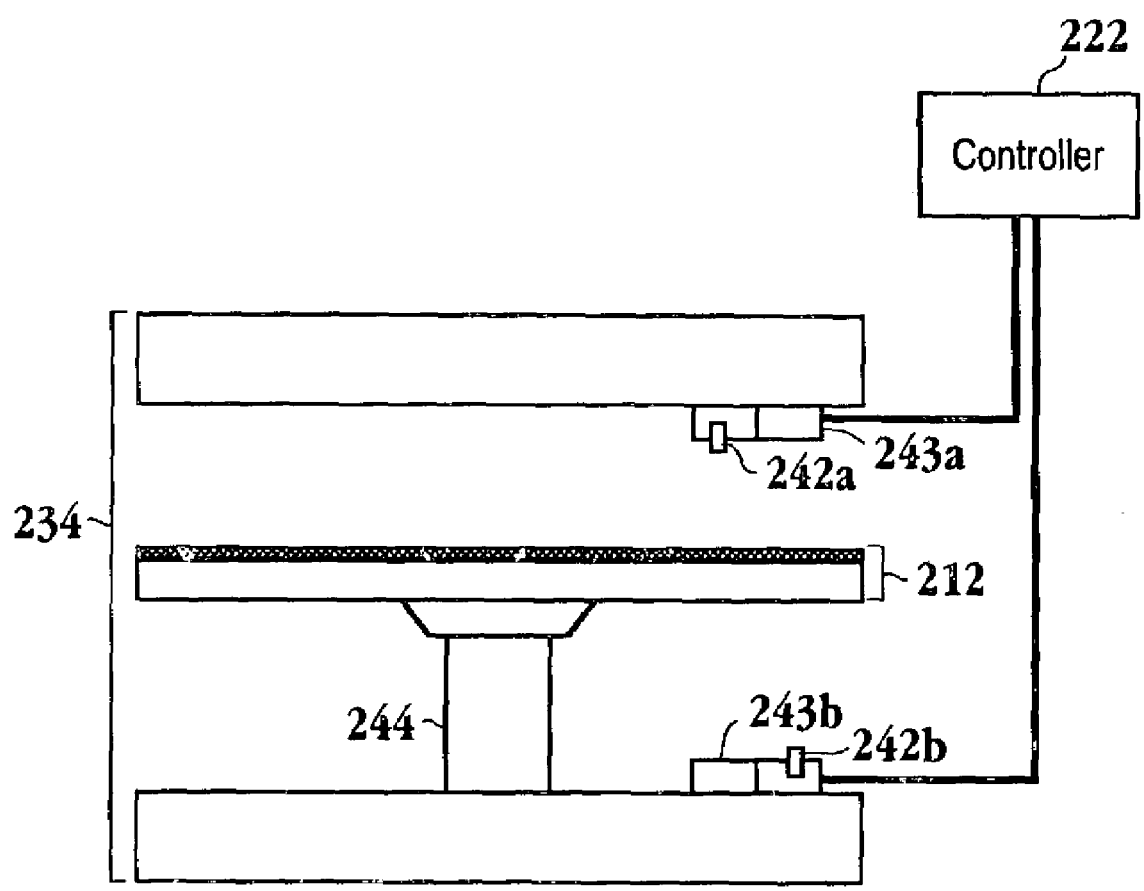
FIG. 9 is a cross sectional view of a simplified schematic of a wafer aligner with an integrated sensor and magnetic field enhancing source in accordance with one embodiment of the invention.

FIG. 9 is a cross sectional view of a simplified schematic of a wafer aligner with an integrated sensor and magnetic field enhancing source in accordance with one embodiment of the invention. Wafer aligner 234 includes spindle 244 that is configured to rotate substrate 212. In one embodiment, substrate 212 is held to spindle 244 through suction applied to a bottom surface of the wafer. Top sensor 242a and bottom sensor 242b are offset from each other, thereby allowing for the placement of magnetic field enhancing sources 243a and 243b to enable the increased sensitivity of the respective sensors. It should be appreciated that the arrangement of the sensors in the embodiment illustrated in FIG. 9 allows for the measurement of a thin film irrespective of the orientation of the wafer. While top sensor 242a and bottom sensor 242b are illustrated as being offset from a center of substrate 212, this is not meant to be restrictive, as the sensors can be positioned in any number of suitable locations over the substrate. In one embodiment where an axis of top sensor 242a is the same as an axis of corresponding bottom sensor 242b, as discussed with reference to FIG. 5.

Each of the sensors of FIG. 9 are in communication with controller 222. In one embodiment, controller 222 is configured to electronically store a thickness profile or some other resistance-based feature characteristic. In one embodiment, the data associated with the resistivity based feature is stored on a suitable storage media associated with controller 222. Of course, any number of sensors can be used to detect a signal indicative of a resistance-based feature characteristic of substrate 212. For example, as substrate 212 is spinning for an alignment process, the sensors can map the thickness profile of the substrate. In one embodiment, controller 222 is a general purpose computer which controls the process operation to which substrate 212 is being delivered. Here, the general purpose computer can store the thickness profile and adjust a recipe for the processing operation prior to or during substrate 212 undergoing the processing operation. That is, the sensors, when placed in the front end of the processing system allows for the customization for each substrate as it is processed, especially in terms of monitoring the thickness of a thin film of the substrate. For example, the process variables for a CMP recipe, such as pressure, belt speed, etc., can be adjusted for a particular substrate. In other words, each process operation can be customized for a particular substrate. One skilled in the art will appreciate that controller 222 may be in communication with another controller or a computer controlling another process operation, wherein the thickness profile is provided to the other controller or computer.

Figure 10:
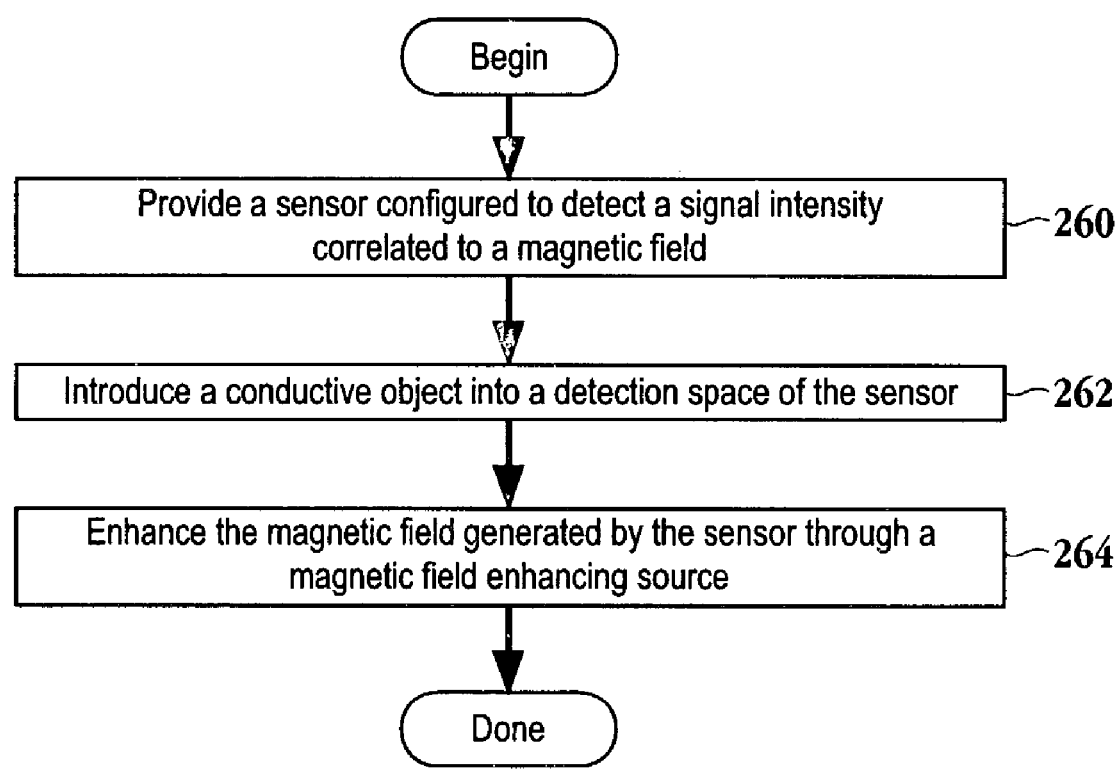
FIG. 10 is a flowchart diagram of the method operations for determining a resistance-based property in accordance with one embodiment of the invention.

FIG. 10 is a flowchart diagram of the method operations for determining a resistance-based feature characteristic in accordance with one embodiment of the invention. The method initiates with operation 260 where a sensor configured to detect a signal intensity correlated to a magnetic field is provided. In one embodiment, the sensor is an eddy current sensor as described above with reference to FIGS. 4–6. The method then advances to operation 262 where an object is introduced into a detection space of a sensor. The detection space of the sensor is the area around the sensor in which the sensor is capable of detecting a signal. In one embodiment, the object is a semiconductor substrate is substantially perpendicular to an axis of the sensor. In another embodiment, multiple sensors are included. In this embodiment, at least two sensors are positioned on opposing, i.e., alternative, sides of the substrate as discussed with reference to FIG. 5. The method then proceeds to operation 264, where the primary magnetic field generated by the sensor is enhanced by a magnetic field enhancing source. As discussed above the magnetic field enhancing source may be a slug of either ferromagnetic material or paramagnetic material or even some combination of both. Additionally, the magnetic field enhancing source may be another sensor, such as an eddy current sensor as discussed with reference to FIG. 6. The enhancement of the primary magnetic field in turn enhances a signal, such as an eddy current signal, thus enhancing the sensitivity and signal to noise ratio of the sensor. In one embodiment, the primary magnetic field is an alternating magnetic field.

It should be appreciated that when integrating the sensor or sensors with a pre-existing station, the particular resistivity based property, such as thickness, doping concentration, etc., of the substrate or object can be determined and electronically stored for a downstream processing operation. In addition, when the substrates are removed from the processing chamber, the thickness of each of the processed substrates can also be scanned to provide feedback as to the results of the processing operation. Accordingly, adjustments can be made to the recipe of the operation based on the feedback. Of course, the post processing results are available for further processing operations also.

In summary, the present invention provides for the enhancement of a magnetic field, which in turn enhances a signal being detected by a sensor. Thus, the sensitivity of the sensor and the signal to noise ratio is increased by the enhancement of the magnetic field. It should be appreciated that in one embodiment, the magnetic field is enhanced by a device that is separate from the sensor, an external source. The increased sensitivity allows the sensor to detect signals that were previously undetectable. Therefore, any resistance-based property of a conductive object placed in the detection space between the magnetic field enhancing source and the sensor can be quantified. Moreover, the signal can be enhanced as described with reference to the above embodiments so that a previously undetectable signal can be measured. For example, the thickness of films less than 2500 Angstroms thick can be measured by an eddy current sensor when used in conjunction with a magnetic field enhancing source.

In one embodiment, the magnetic field enhancing source is a ferromagnetic or paramagnetic slug. In another embodiment, a second sensor is the magnetic field enhancing source. When the second sensor is the magnetic field enhancing source, a phase shift is applied so that the two sensors are out of phase. Here, the phase of the magnetic field generated by the second sensor is 180° off of the phase of the magnetic field of the first sensor so as to not have a suppressing effect. That is, one sensor overturns a wave of the signal by 180° to eliminate suppression of the signal. While the embodiments described above refer specifically to eddy current sensors used to measure thin film thickness, it should be appreciated that any resistance-based property may be measured. Furthermore, the invention described herein can be incorporated to numerous semiconductor processing tools for processes, such as CMP, plasma etch, layer deposition and other processes requiring the thickness of a layer of a substrate to be characterized. Within these processing tools, the magnetic field/eddy current enhancing source can be incorporated easily. For example, with respect to etch and deposition tools, the substrate support, i.e., chuck, can either be composed of material having magnetic field enhancing properties or can include inserts having these properties. It will be apparent to one skilled in the art that the chuck may be an electrostatic chuck, a vacuum chuck a mechanical chuck, etc.

However, as mentioned above, the invention can be expanded to determine any suitable resistance-based property of a conductive object. That is, in addition to determining the thickness of a thin film on a substrate or the thickness of the substrate itself, the embodiments described herein can be used to determine dopant concentration, identify film stack composition, thin metal film integrity, surface roughness, distribution of impurities, grain size distribution, etc. In essence, the magnetic field/eddy current enhancing source enables a wide range of resistance-based properties to be ascertained for a conductive object placed in a sensor detection space. While some of the examples described herein are directed toward semiconductor manufacturing applications, the embodiments are not limited to those applications. Any application requiring the information provided by the resistance-based properties can take advantage of the sensitivity enhancement embodiments described herein.

One embodiment of the invention described herein, uses permalloy as a the magnetic field enhancing source. One skilled in the art will appreciate that permalloy refers generally to a group of alloys of high magnetic permeability consisting of nickel and iron and having a composition of $Ni_xFe_y$. In one embodiment, the iron and the nickel account for between about 40% and about 80% of the composition of the permalloy. In another embodiment, the permalloy includes small amounts of other elements, such as molybdenum, copper, chromium or tungsten.

The invention has been described herein in terms of several exemplary embodiments. Other embodiments of the invention will be apparent to those skilled in the art from consideration of the specification and practice of the invention. The embodiments and preferred features described above should be considered exemplary, with the invention being defined by the appended claims.

What is claimed is:

1. A method for determining a resistance-based property, comprising:
   providing a sensor configured to detect a signal intensity correlated to a magnetic field;
   introducing a conductive object into a detection space of the sensor; and
   enhancing a primary magnetic field generated by the sensor through a magnetic field enhancing source configured to move and support the conductive object to increase a sensitivity and signal to noise ratio of the sensor, wherein the signal intensity is indicative of a thickness of one of a film disposed over a surface of the conductive object and the conductive object.

2. The method of claim 1, wherein the sensor is an eddy current sensor.

3. The method of claim 1, wherein the resistance-based property is selected from the group consisting of layer thickness, dopant concentration, film stack composition, thin metal film integrity, surface roughness, surface layer integrity, distribution of impurities, and grain size distribution.

4. The method of claim 1, wherein the thickness of the thin film is less than about 2500 Angstroms.

5. The method of claim 1, wherein the method operation of enhancing a primary magnetic field generated by the sensor through a magnetic field enhancing source to increase a sensitivity and a signal to noise ratio of the sensor includes,
locating the magnetic field enhancing source on an alternative side of the conductive object opposing the sensor.

6. The method of claim 2, wherein the magnetic field enhancing source is selected from the group consisting of ferromagnetic material, paramagnetic material and an other eddy current sensor.

7. The method of claim 6, wherein the ferromagnetic material is a permalloy-based material.

8. The method of claim 1 wherein the conductive object is a semiconductor substrate.

9. The method of claim 8, wherein the film is a copper film.

10. An apparatus for measuring resistance-based properties of a conductive object, comprising:
a sensor configured to detect a signal produced by a magnetic field;
a magnetic field enhancing source, the magnetic field enhancing source positioned relative to the sensor to enable a conductive object to be placed in a detection space between the sensor and the magnetic field enhancing source, the magnetic field enhancing source increasing a sensitivity of the sensor; and
a support for the conductive object, the support providing rotational and linear movement for the conductive object within the detection space.

11. The apparatus of claim 10, wherein the sensor is an eddy current sensor.

12. The apparatus of claim 11, wherein an intensity of the signal corresponds to one of a thickness of a layer of the conductive object, a dopant level of the conductive object, an integrity feature of the conductive object, a surface roughness of the conductive object an amount of impurities in the conductive object and a size of grains in the conductive object.

13. The apparatus of claim 12, wherein the integrity feature of the conductive object includes integrity features selected from the group consisting of scratches and cracks.

14. The apparatus of claim 10, wherein the magnetic field enhancing source is composed of a material selected from the group consisting of ferromagnetic material and paramagnetic material.

15. The apparatus of claim 11, wherein the magnetic field enhancing source is an other eddy current sensor opposing an other side of the object and substantially aligned with the eddy current sensor, the other eddy current sensor generating a second magnetic field that is synchronized with the magnetic field of the eddy current sensor.

16. The apparatus of claim 12, wherein the layer of the conductive object is a metal layer.

17. The apparatus of claim 12, wherein the thickness of the layer is between about 2500 Angstroms and about 0 Angstroms.

18. A system enabled to determine a thickness of a layer of an object through a signal generated by a magnetic field, comprising:
an eddy current sensor;
a magnetic field enhancing source positioned to define a detection space between the eddy current sensor and the magnetic field enhancing source, the magnetic field enhancing source intersecting an axis of the eddy current sensor;
a base configured to support an object such that the object is positioned within the detection space between the eddy current sensor and the magnetic field enhancing source, the base providing rotational and linear movement for the object; and
a controller in communication with the eddy current sensor, the controller configured to output a thickness of a layer of the object from a signal detected by the eddy current sensor, wherein the sensitivity of the eddy current sensor is increased by the magnetic field enhancing source.

19. The system of claim 18, wherein the magnetic field enhancing source is an other eddy current sensor placed opposing an alternative side of the object, the other eddy current sensor substantially aligned and electrically synchronized with the eddy current sensor.

20. The system of claim 18, wherein the magnetic field enhancing source is one of a ferromagnetic material and a paramagnetic material.

21. The system of claim 20, wherein the ferromagnetic material is selected from the group consisting of permalloy, iron containing compounds, nickel containing compounds and cobalt containing compounds.

22. The system of claim 20, wherein the paramagnetic material is selected from the group consisting of magnesium, gadolinium and aluminum.

23. The system of claim 18, wherein the controller is a general purpose computer.

24. The system of claim 18, wherein the support is associated with one of a mapper and an aligner of a semiconductor fabrication tool.

25. The system of claim 18, wherein the support is a wafer carrier, the wafer carrier having the eddy current sensor embedded therein, the magnetic field enhancing source being a stainless steel backing of a polishing pad.

26. A system enabled to determine a thickness of a layer of a substrate, comprising:
a substrate support configured to support a bottom surface of a substrate, the substrate support including a magnetic field enhancing source, the substrate support is selected from the group consisting of a vacuum chuck, an electrostatic chuck, and a mechanical chuck;
an eddy current sensor positioned above the substrate support; and
a controller in communication with the eddy current sensor, the controller configured to output a thickness of a layer of the substrate from a signal detected by the eddy current sensor, wherein the sensitivity of the eddy current sensor to the signal is increased by the magnetic field enhancing source.

27. The system of claim 26, wherein the magnetic field enhancing source is a compound consisting essentially of nickel and iron.

* * * * *